US009072299B2

(12) United States Patent
Esculier

(10) Patent No.: US 9,072,299 B2
(45) Date of Patent: Jul. 7, 2015

(54) INSECT REPELLENT COMPOSITION

(75) Inventor: Marc Esculier, Neuilly sur Seine (FR)

(73) Assignee: DAKEM, Courbevoie (FR)

( * ) Notice: Subject to any disclaimer, the term of this patent is extended or adjusted under 35 U.S.C. 154(b) by 152 days.

(21) Appl. No.: 13/256,044

(22) PCT Filed: Mar. 11, 2010

(86) PCT No.: PCT/IB2010/051050
§ 371 (c)(1),
(2), (4) Date: Nov. 21, 2011

(87) PCT Pub. No.: WO2010/103478
PCT Pub. Date: Sep. 16, 2010

(65) Prior Publication Data
US 2012/0065229 A1 Mar. 15, 2012

(30) Foreign Application Priority Data
Mar. 13, 2009 (FR) ...................... 09 51590

(51) Int. Cl.
A01N 43/40 (2006.01)
(52) U.S. Cl.
CPC ...................... *A01N 43/40* (2013.01)
(58) Field of Classification Search
CPC ....................................... A01N 43/40
USPC ...................................... 514/315
See application file for complete search history.

(56) References Cited

U.S. PATENT DOCUMENTS 6,180,127 B1 * 1/2001 Calton et al. .................. 424/409
2004/0170660 A1 9/2004 Wendel et al.

FOREIGN PATENT DOCUMENTS

WO 0243489 A 6/2002
WO 0243490 A 6/2002
WO 03020232 A 3/2003

OTHER PUBLICATIONS

Chemwatch, picaridin, Issue Date Jan. 2007.*
International Search Report in International Application PCT/IB2010/051050, having a mailing date of Jul. 13, 2010 and English Translation.
Written Opinion in International Application PCT/IB2010/051050, having a mailing date of Jul. 13, 2010 and English Translation.
French Written Opinion of French Application No. 09 51590, which corresponds to International Written Opinion of International Application No. PCT/IB2010/051050, for which an English language translation is included.
French Search Report issued by French Patent Office in priority application, FR 09 51590, having a date of Oct. 1, 2009.

* cited by examiner

*Primary Examiner* — Golam M M Shameem
(74) *Attorney, Agent, or Firm* — Jones Robb, PLLC

(57) ABSTRACT

The present invention relates to an insect repellent composition containing the following active insect-repellent material in a physiologically acceptable medium: at least 1-methylpropyl(2-(2-hydroxyethyl)piperidine-1-carboxylate, said active material being used with at least one copolymer of vinylpyrrolidone and of a linear alkyl, having at least 16 carbon atoms, as a film-forming agent.
The invention also relates to an insect-repelling method using said composition.

13 Claims, No Drawings

INSECT REPELLENT COMPOSITION

This is a national stage application of PCT/IB2010/051050, filed internationally on Mar. 11, 2010, which claims priority to French Application No. 09 51590, filed on Mar. 13, 2009.

The subject of the present invention is a biting insect, in particular mosquito, repellent composition.

It is known practice for people to protect themselves against insects by applying active repellent agents to the skin. However, most of the solutions for protecting the body against biting insects have a limited effectiveness time since the latter is often affected by the moisture of the environment. For example, the high degree of humidity in tropical zones leads to a considerable increase in sweating in individuals, which has the effect of causing a premature elimination of the anti-insect composition applied to the surface of their skin. Similarly, the direct contact of water, for example during swimming, with such a composition applied at the surface of the skin, is also of course prejudicial.

This deficiency in water resistance, shown by a large number of anti-insect compositions, therefore requires attention by the individual treated, who must apply a new coat of composition after any prolonged contact with water or significant sweating.

In order to overcome this deficiency, the use of film-forming agents, for instance vinylpyrrolidone copolymers, in order to increase the moisture resistance of these anti-insect compositions, has been proposed.

The present invention, for its part, aims to propose a novel anti-insect composition which simultaneously has good insect repellent properties and a particularly increased resistance with regard to moisture.

More specifically, the present invention proposes a composition which provides long-lasting insect repellent protection, including under extreme climatic conditions and/or after swimming for a short period of time.

The inventors have thus discovered, surprisingly, that the combination of a particular film-forming agent and of a latest-generation active insect repellent material, such as 1-methylpropyl(2-(2-hydroxyethyl)piperidine-1-carboxylate, makes it possible to obtain such a composition.

The film-forming agent under consideration according to the invention in fact efficiently provides binding of the active repellent material and prevents elimination thereof in contact with water.

A first subject of the invention is therefore an insect repellent composition comprising, in a physiologically acceptable medium, as active insect repellent material, at least 1-methylpropyl(2-(2-hydroxyethyl)piperidine-1-carboxylate, said active agent being used with at least one copolymer of vinylpyrrolidone and of a linear alkyl containing at least 16 carbon atoms.

A second subject of the invention is a method for repelling insects with respect to a substrate, and more particularly the skin, comprising the application to said substrate of an effective amount of at least one composition as defined in the present invention.

This substrate is advantageously the skin; however, it may also be an item of clothing or other textile material intended to protect the skin against insects.

As emerges from the examples which follow, the copolymer under consideration according to the invention as film-forming agent is advantageous in many respects.

First of all, biological tests for effectiveness under tropical conditions have confirmed an effectiveness of 8 hours without any bite, on a composition which combines it with the active anti-insect agent retained according to the invention. These results therefore show that the use of this specific copolymer makes it possible to guarantee an increased moisture resistance of the anti-insect formulation and therefore confers on this formulation a "waterproof" nature. They also demonstrate that this specific film-forming agent does not, moreover, affect the reactivity of 1-methylpropyl(2-(2-hydroxyethyl)piperidine-1-carboxylate with regard to insects. The latter remains effective at doses conventionally used.

What is more, the copolymer under consideration according to the invention is found to be easy to formulate. Thus, it does not require an excessive amount of oil for processing thereof. Consequently, it can be formulated in a non-greasy aqueous emulsion (no greasy effect, no tacky or drying-out effect, stain-free). In addition, it can be easily removed with soapy water.

Finally, this copolymer is particularly advantageous in terms of innocuousness and, in this respect, is compatible with application to the skin, even the eyelids and the lips.

Advantageously, the composition according to the invention is in the form of an oil-in-water emulsion.

More particularly, this composition is waterproof.

Active Repellent Material

The repellent composition according to the present invention contains, as active insect repellent material, at least 1-methylpropyl(2-(2-hydroxyethyl)piperidine-1-carboxylate or a salt thereof.

1-Methylpropyl(2-(2-hydroxyethyl)piperidine-1-carboxylate is also known as ICARIDIN. It is currently sold under the name SALTIDIN by the company Saltigo.

A composition according to the invention may advantageously contain from 10 to 25% and preferably from 15 to 22% by weight of 1-methylpropyl(2-(2-hydroxyethyl)piperidine-1-carboxylate, relative to its total weight.

Of course, a composition according to the invention may also comprise another additional active material, in particular with a repellent effect. Said material may in particular be chosen from N,N-diethyl-3-methylbenzamide (DEET), ethyl butylacetylaminopropionate (IR3535), citronella or else geraniol.

Film-Forming Agent

The repellent composition according to the invention also contains at least one copolymer of vinylpyrrolidone and of a linear alkyl containing at least 16 carbon atoms, as film-forming polymer. According to one preferred embodiment variant, the linear alkyl unit is advantageously a $C_{16}$ to $C_{18}$ linear alkyl chain and preferably a $C_{16}$ linear alkyl chain.

More specifically, the copolymer under consideration according to the invention is a copolymer of vinylpyrrolidone and of hexadecene or a copolymer of vinylpyrrolidone and of eicosene.

It may in particular be the following commercial products, Antaron V-216 and Antaron V-220 sold by ISP (International Specialty Products).

The composition may advantageously contain from 0.1 to 15% and preferably from 1 to 10% by weight of copolymers of vinylpyrrolidone and of a $C_{16}$ linear alkyl, relative to its total weight.

Other additional film-forming agents may be present jointly with the copolymer under consideration according to the invention.

By way of nonlimiting illustration of these supplementary film-forming agents, mention may in particular be made of Tricontanyl PVP, hydrogenated diinoley/dimethyl carbonate copolymer, acrylate copolymers or else acrylate/alkyl methacrylate copolymers.

For obvious reasons, the Icaridin and the film-forming agent required according to the invention are formulated in a physiologically acceptable medium.

Thus, a composition according to the invention advantageously comprises, as physiologically acceptable medium, an aqueous medium and in particular water, preferably demineralized water. This aqueous medium may be present in an amount ranging up to 80% and preferably from 40 to 80% by weight, relative to its total weight.

The composition according to the invention may also comprise one or more silicone oils. By way of examples of silicone oils that are suitable for the invention, mention may in particular be made of dimethicone, phenyl trimethicone, $C_{26}$-$C_{28}$ alkyl methicone, cetyl dimethicone and stearyl dimethicone, and mixtures thereof.

These oils are advantageous from the formulation point of view. They also give the formulations containing them a pleasant gliding nature on application. What is more, some of these oils also have an emollient function.

This silicone oil is preferably dimethicone.

Advantageously, a composition according to the invention may comprise from 0.1 to 10% and preferably from 1 to 5% by weight of silicone oil(s), relative to its total weight.

The composition is advantageously in the form of an emulsion, in particular an oil-in-water emulsion.

With regard to its emulsion-type formulation, a composition according to the invention generally advantageously comprises one or more emulsifiers. This emulsifier may be chosen from sucrose esters, glycerol fatty esters, fatty acids, and ethoxylated fatty alcohols, and mixtures thereof.

The composition according to the invention may also advantageously comprise one or more humectants. This humectant may be chosen from glycols, such as glycerol, propylene glycol or else dipropylene glycol, and waxes, such as shea butter or beeswax, and mixtures thereof.

The humectant is preferably glycerol.

Likewise, a composition according to the invention may also comprise one or more emollients. By way of examples of emollients, mention may most particularly be made of $C_{12}$ to $C_{is}$ alkyl benzoate, isopropyl palmitate, isopropyl myristate, ethylhexyl palmitate, plant oils, mineral oils and silicones, and mixtures thereof.

The emollient is preferably $C_{12}$ to $C_{15}$ alkyl benzoate.

The composition according to the invention may also comprise one or more gelling agents chosen from sucrose palmitate, glyceryl stearate and glyceryl stearate citrate, and mixtures thereof.

According to one embodiment variant, a composition according to the invention may also comprise an active anti-UV agent capable of conferring on said composition protective properties with regard to UV exposure.

The composition according to the invention may also comprise the conventional additives in the field, for instance those chosen from the nonexhaustive list such as chelating agents, preservatives, pH regulators and fragrances.

As specified above, the composition is advantageously in the form of an emulsion, in particular an oil-in-water emulsion. This composition may be in the form of a cream, a milk or a gel, which can be applied as appropriate by spraying.

The present invention is also directed toward the use of an insect repellent composition according to the invention. More specifically, it is directed toward a method for repelling insects from skin, comprising the application of a sufficient amount of a composition as defined according to the present invention to a substrate, such as the skin, or a substrate intended to be brought into contact with said skin.

The examples and figures which follow hereinafter are given by way of nonlimiting illustration of the invention.

Example 1

Topical Formulation According to the Invention

| TRADE NAME | INCI NAME | FUNCTION | % BY WEIGHT |
| --- | --- | --- | --- |
| Saltidin (Icaridin) sold by Saltigo | Hydroxyethyl isobutyl piperidine carboxylate | Active mosquito repellent agent | 20 |
| Antaron V 216 sold by ISP (International Specialty Products) | VP/Hexadecene copolymer | Film-forming agent | 5 |
| DC 200 Fluid 100 CST | Dimethicone | Silicone | 2 |
| Tegosoft TN | $C_{12}$-$_{15}$ Alkyl Benzoate | Emollient | 2 |
| Demineralized water | Aqua | Solvent | Qs |
| Glycerol | Glycerin | Emollient | 5 |
| Arlatone V 175 | Sucrose Palmitate, Glyceryl Stearate, Glyceryl Stearate Citrate, Sucrose Mannan, Xanthan Gum | Emulsifier | 1.10 |
| Carbopol EDT 2050 | Carbomer | Gelling agent | 0.10 |
| Disodium EDTA | Disodium EDTA | Chelating agent | 0.10 |
| Euxyl PE9010 | Phenoxyethanol, Ethylhexylglycerin | Preservative | 0.80 |
| Triethanolamine | Triethanolamine | pH regulator | 0.10 |
| Yakusa fragrance | Fragrance | Fragrance | 1.50 |

Example 2

The effectiveness of the formulation of example 1 was assessed with respect to *Anopheles stephensi* mosquitoes.

In the absence of a French standard, the method follows the following guidelines:
  WHO General Recommendations: WHO/CDS/WHOPES/ 2001.2
  ASTM (American Society for Testing and Materials): ASTM E951-94 (laboratory)

The tests are carried out with females of mosquitoes raised in the laboratory: *Anopheles stephensi* (strain ORSTOM).

The females used for the tests are 6 to 10 days old and were not fed during the preceding 24 hours (no blood meal) in order to increase their aggressiveness.

The blood meal target is a hairless mouse kept in a containment cage (eyes protected) and which is coated with a test product (0.1 g/60 cm$^2$). Application is by pipette.

30 minutes after application of the product, the mouse is then placed in a cage containing approximately 200 females (prior elimination of the males by food gradient).

The test lasts 5 minutes and, during this period, the number of mosquitoes which have landed on the mouse ("landing effect"), and then the number of actual bites (unless there is a clear ineffectiveness), are recorded.

The test is stopped once there have been 5 actual bites.

The test is recommenced with new batches of mosquitoes, after 2, 4, 6, 7, 8 and 9 hours following application according to the limit of persistence of the product (the mouse is released between times).

The same test is carried out with mice having received no treatment, in order to verify the natural tendency of the mosquitoes to bite. It is verified that there are at least 10 landings and more than 5 bites in 30 seconds in order to validate the test.

The test is stopped after 5 bites ("stop") in the table of data represented below.

The "landing" data correspond to the number of mosquitoes landing on the zone treated, but which leave again without having bitten. This datum can provide information on the limit of persistence of the products, since the mosquitoes increasingly approach the treated zone until the repellent effect is insufficient and there is actual biting.

During and between these sessions, the mice are kept in a "tropical" atmosphere under controlled conditions at 27±1° C. and 70±5% relative humidity.

The cages are changed at each unit test and place three meters apart.

Three repeats are carried out per test formulation and on three different mice, i.e. nine unit tests per formulation.

The results are given in table I hereinafter.

TABLE I

| ANOPHELES STEPHENSI | mouse | rep. | T0 + 2H | | T0 + 4H | | T0 + 6H | | T0 + 7H | | T0 + 8H | | T0 + 9H | |
|---|---|---|---|---|---|---|---|---|---|---|---|---|---|---|
| | | | B | L | B | L | B | L | B | L | B | L | B | L |
| Formulation Example 1 | 1 | 1 | 0 | 0 | 0 | 0 | 0 | 0 | 0 | 0 | 0 | 3 | stop | stop |
| | | 2 | 0 | 0 | 0 | 0 | 0 | 0 | 0 | 0 | 0 | 1 | stop | stop |
| | | 3 | 0 | 0 | 0 | 0 | 0 | 0 | 0 | 1 | 0 | 0 | stop | stop |
| | 2 | 1 | 0 | 0 | 0 | 0 | 0 | 0 | 0 | 0 | 0 | 2 | stop | stop |
| | | 2 | 0 | 0 | 0 | 0 | 0 | 0 | 0 | 0 | 0 | 3 | stop | stop |
| | | 3 | 0 | 0 | 0 | 0 | 0 | 0 | 0 | 0 | 0 | 2 | slop | stop |
| | 3 | 1 | 0 | 0 | 0 | 0 | 0 | 0 | 0 | 0 | 0 | 4 | stop | stop |
| | | 2 | 0 | 0 | 0 | 0 | 0 | 0 | 0 | 1 | 0 | 3 | stop | stop |
| | | 3 | 0 | 0 | 0 | 0 | 0 | 0 | 0 | 0 | 0 | 2 | stop | stop |
| Test without product | 1 | 1 | stop | stop | stop | stop | stop | stop | stop | stop | stop | stop | stop | stop |
| | | 2 | stop | stop | stop | stop | stop | stop | stop | stop | stop | stop | stop | stop |
| | | 3 | stop | stop | stop | stop | stop | stop | stop | stop | stop | stop | stop | stop |
| | 2 | 1 | stop | stop | stop | stop | stop | stop | stop | stop | stop | stop | stop | stop |
| | | 2 | stop | stop | stop | stop | stop | stop | stop | stop | stop | stop | stop | stop |
| | | 3 | slop | stop | slop | stop | slop | stop | slop | stop | slop | stop | slop | stop |
| | 3 | 1 | stop | stop | stop | stop | stop | stop | stop | stop | stop | stop | stop | stop |
| | | 2 | stop | stop | stop | stop | stop | stop | stop | stop | stop | stop | stop | stop |
| | | 3 | stop | stop | stop | stop | stop | stop | stop | stop | stop | stop | stop | stop |

B: number of bites
rep: repeat
L.: "landing" = number of mosquitoes landing without biting on the treated zone
stop = the test is stopped when more than 5 bites are observed It may be noted that, under the conditions of these tests, with the samples provided, insect strains and method under consideration, the formulation showed a highly significant repellent effect with respect to *Anopheles stephensi*. The persistence of action is 8 hours.

The invention claimed is:

1. An insect repellent composition comprising, in a physiologically acceptable medium, as active insect repellent material, at least 20% by weight of 1-methylpropyl(2-(2-hydroxyethyl)piperidine-1-carboxylate, said active insect repellent material being used in an aqueous medium with about 5% by weight of at least one copolymer of vinylpyrrolidone and hexadecene and at least one silicone oil.

2. The repellent composition of claim 1, comprising from 40 to 80% by weight of said aqueous medium, relative to its total weight.

3. The repellent composition of claim 1, comprising one or more silicone oils chosen from dimethicone, phenyl trimethicone, $C_{26}$-$C_{28}$ alkyl methicone, cetyl dimethicone and stearyl dimethicone, and mixtures thereof.

4. The repellent composition of claim 1, comprising from 0.1 to 10% by weight of silicone oil(s), relative to its total weight.

5. The repellent composition of claim 1 further comprising one or more humectants chosen from glycols, waxes and mixtures thereof.

6. The repellent composition of claim 1 further comprising one or more emollients chosen from the esters $C_{12}$ to $C_{15}$ alkyl benzoate, isopropyl palmitate, isopropyl myristate, ethylhexyl palmitate, plant oils, mineral oils and silicones, and mixtures thereof.

7. The repellent composition of claim 1 wherein the repellent composition is in the form of an emulsion.

8. The repellent composition of claim 1 further comprising one or more emulsifiers chosen from sucrose esters, glycerol fatty esters, fatty acids and ethoxylated fatty alcohols, and mixtures thereof, and/or one or more gelling agents chosen from sucrose palmitate, glyceryl stearate and glyceryl stearate citrate, and mixtures thereof.

9. The repellent composition of claim 1 wherein the repellent composition is waterproof.

10. The repellent composition of claim 1 wherein the repellent composition is in the form of one of a cream, a milk or a gel.

11. A method for repelling insects from the skin, comprising the step of applying a sufficient amount of the repellent composition of claim 1 to the skin.

12. The repellent composition of claim 1, comprising from 1 to 5% by weight of silicone oil(s), relative to its total weight.

13. The repellent composition of claim 5, comprising one or more of glycerol, propylene glycol, dipropylene glycol, shea butter, and beeswax, and mixtures thereof.

* * * * *